(12) United States Patent
Reimann et al.

(10) Patent No.: US 7,029,680 B1
(45) Date of Patent: Apr. 18, 2006

(54) DELIVERY OF IMMUNOGENIC MOLECULES VIS HBSAG PARTICLES

(75) Inventors: Jörg Reimann, Ringstrasse 88, D-89081, Ulm-Lehr (DE); Yechezkel Barenholz, Jerusalem (IL); Dvorah Diminsky, Jerusalem (IL); Reinhold Schirmbeck, Krumbach (DE)

(73) Assignees: Yissum Research Development Company of the Hebrew University of Jerusalem, Jerusalem (IL); Jorg Reimann, Ulm-Lehr (DE)

( * ) Notice: Subject to any disclaimer, the term of this patent is extended or adjusted under 35 U.S.C. 154(b) by 0 days.

(21) Appl. No.: 09/241,595

(22) Filed: Feb. 2, 1999

Related U.S. Application Data

(60) Provisional application No. 60/073,476, filed on Feb. 3, 1998.

(51) Int. Cl.
    *A61K 39/385* (2006.01)
    *A61K 39/29* (2006.01)
    *A61K 38/00* (2006.01)

(52) U.S. Cl. ............... 424/196.11; 424/227.1; 424/189.1; 424/85.1; 514/2; 514/44

(58) Field of Classification Search .......... 514/2; 424/85.1
    See application file for complete search history.

(56) References Cited

U.S. PATENT DOCUMENTS 5,039,522 A * 8/1991 Neurath .............. 424/89

FOREIGN PATENT DOCUMENTS

| EP | 326109 | 2/1989 |
| EP | 0 326 109 A2 | 8/1989 |
| WO | WO 98/52962 | 11/1998 |

OTHER PUBLICATIONS

Yasutomi et al. (1995) J. Virol., vol. 69(4), 2279-2284, 1995.*
Fox (1994) Bio/Technology, vol. 12, 128, 1994.*
Abbas et al. (1996) Nature, vol. 383, 787-793, 1996.*
Golding et al. (1994) Am. J. Trop. Med. Hyg., vol. 50(4), 33-40, 1994.*

Michel et. al.; Recombinant hepatitis B surface antigen as a carrier of human immunodefiency virus epitopes, 1993, Institut Pasteur/Elsevier 144: 263-267.*
Schirmbeck et al. (1996) Intervirology, vol. 39 (1), 111-119.*
Clarke, B.E. et al., "Improved Immunogenicity of a Peptide Epitope after Fusion to Hepatitis B Core Protein," *Nature* 330:381 (1987).
Delpeyroux, F. et al., "A Poliovirus Neutralization Epitope Expressed on Hybrid Hepatitis B Surface Antigen Particles," *Science* 233:472 (1986).
Diminsky, D. et al., "Comparison Between Hepatitis B Surface Antigen (HBsAg) Particles Derived from Mammalian Cells (CHO) and Yeast Cells (*Hansenula polymorpha*): Composition, Structure and Immunogenicity," *Vaccine* 15:6/7:637-647 (1997).
Francis, M.J. et al., "Immunological Properties of Hepatitis B Core Antigen Fusion Proteins," *Proc. Natl. Acad. Sci. USA* 87:2545-2549 (1990).
Schirmbeck, R. et al., "Immunization with Soluble Hepatitis B Virus Surface Protein Elicits Murine H-2 Class I-Restricted $CD8^+$ Cytotoxic T Lymphocyte Responses In Vivo," *J. Immunol.* 152(3):1110-1119 (1994).
Davis, H., et al., "CpG DNA is a potent enhancer of specific immunity in mice immunized with recombinant hepatitis B surface antigen." The Journal of Immunology 160(2):870-876(1998).
International Search Report for Application No. PCT/IL99/00060.
Qu, D., et al., "Humoral immune response enhanced by immunization with anti-HBs and HBsAAg complex plus DNA vaccine." Chem. Abstracts 129(16): 539, abstract No. 201834 (1998).
Qu et al., Humoral immune response enhancer by immunization with anti-HBs and HbsAg complex plus DNA vaccine, Chemical Abstracts, p. 539.

(Continued)

*Primary Examiner*—Anne Marie S. Wehbe'
(74) *Attorney, Agent, or Firm*—Browdy and Neimark, PLLC

(57) ABSTRACT

Compositions of HBsAg particles having biologically active molecules contained in the particles, and methods of their use, e.g. in stimulating enhanced immune responses, are described. Antigenic peptides contained in HBsAg particles were found to produce a CTL response where none was elicited by the peptide alone. Encapsulation of immunostimulating molecules, such as cytokines, greatly enhanced the CTL response evoked by the HBsAg particles themselves.

22 Claims, 6 Drawing Sheets

OTHER PUBLICATIONS

Figures 1A, 1B:
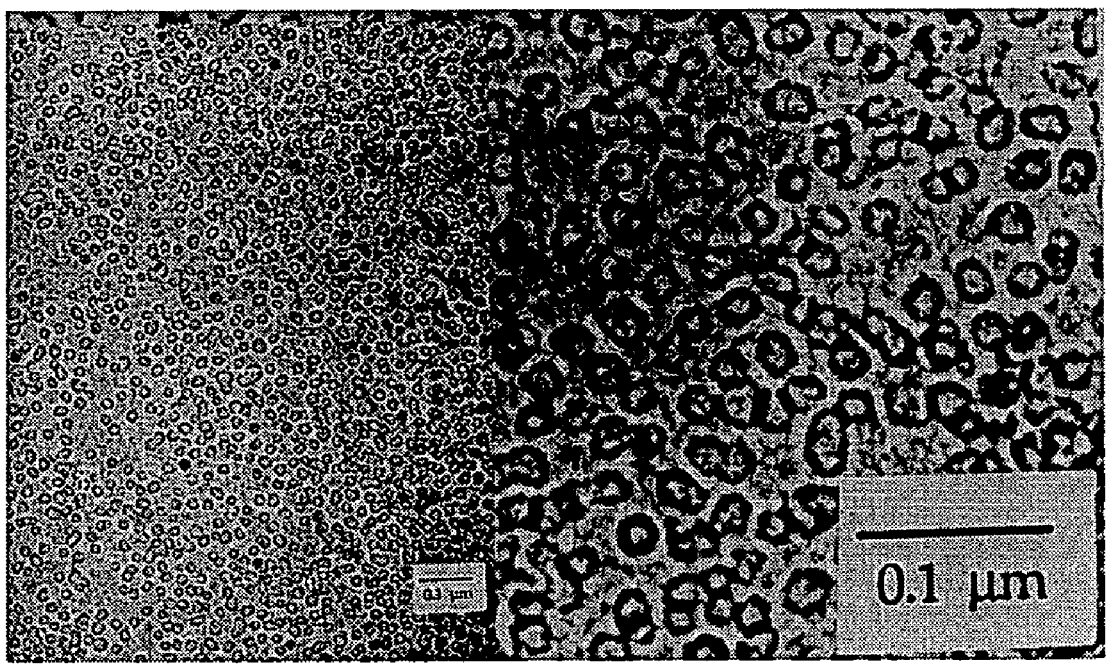
Figure 2A:
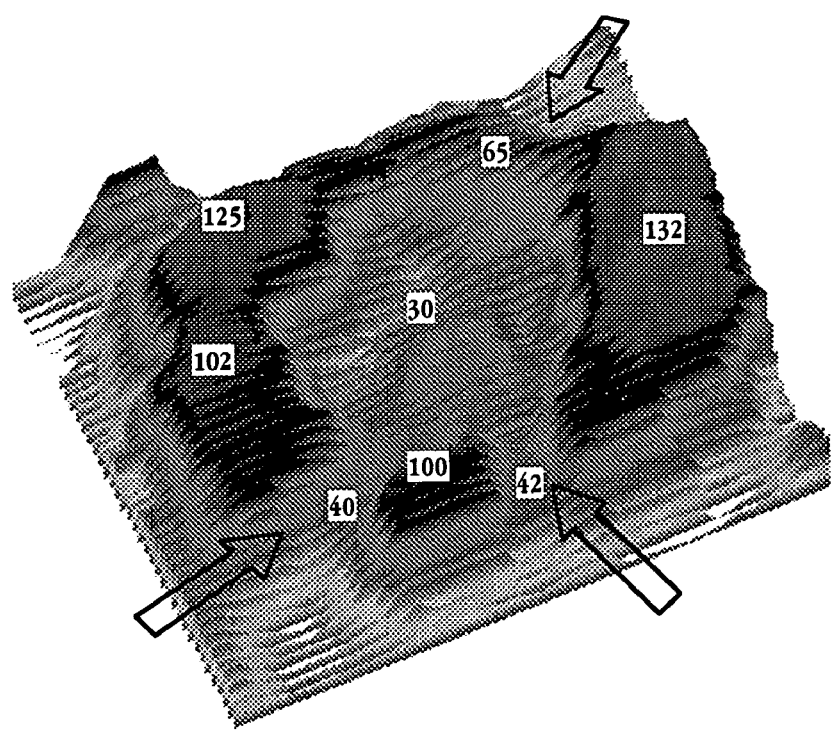
Figure 2B:
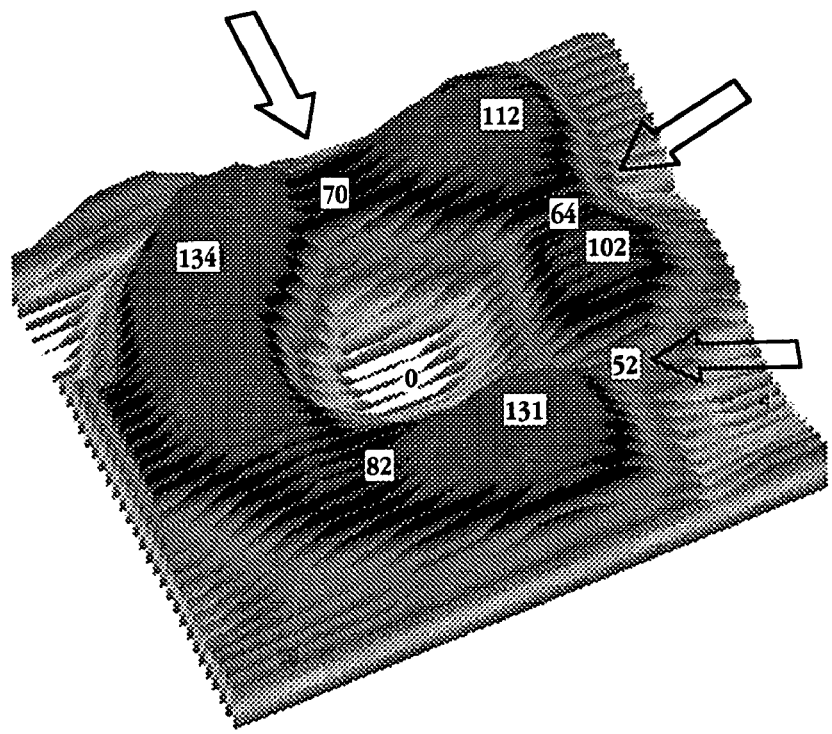

Davis et al., CpG DNA is a potent enhancer of specific immunity in mice immunized with recombinant Hepatitis B surface antigen, *The Journal of Immunology*, 160:870-876 (1998).

Schirmbeck et al., Nucleic acid vaccination primes hepatitis B virus surface antigen-specific cytotoxic T Hymphocytes in nonresponder mice, *Journal of Virology*, 5929-5934 (1995).

Schirmbeck et al., Enhancing the immunogenicity of exogenous Hepatitis B surface antigen-based vaccines for MHC-O-restricted T cells, *Biol. Chem.*, 380:285-291 (1999).

Puzo, The carbohydrate- and lipid- containing cell wall of mycobacteria, phenolic glycolipids: structure and immunological properties, *Microbiology*, 17:305-327.

Yamamoto et al., Ability of oligonucleotides with certain palindromes to induce interferon production and augment natural killer cell activity is associated with their base length, *Antisense Research and Development*, 4:119-122 (1994).

Felgner et al., Asymmetric incorporation of trisialoganglioside into dipalmitoylphosphatidylcholine vesicles, *Biochemistry*, 20:2168-2172 (1981).

Wong et al., Glycolipid transfer protein from bovine brain, *Biochemistry*, 23:6498-6505 (1984).

Wooldridge et al., Immunostimulatory oligodeoxynucleotides containing CpG motifs enhance the efficacy of monoclonal antibody therapy of lymphoma, *Blood*, 89(8):2994-2998 (1997).

Nguyen et al., Constrasting effects of T cell growth factors on T cell responses to melanoma in vitro, *Cancer Immunol. Immunother.*, 43:345-354 (1997).

Weiner et al., Immunostimulatory oligodeoxynucleotides containing the CpG motif are effective as immune adjuvants in tumor antigen immunization, *Proc. Natl. Acad. Sci. USA*, 94:10833-10837 (1997).

Lowry et al., Protein measurement with the folin phenol reagent, *Department of Pharmacology*, 265-275 (1951).

Yamamoto et al., Unique palindromic sequences in synthetic oligonucleotides are required to induce INF and augment INF-mediated natural killer activity, *The Journal of Immunology*, 148:4072-4076 (1992).

Geissler et al., Enhancement of cellular and humoral immune responses to Hepatitis C virus core protein using DNA-based vaccines augmented with cytokine-expressing plasmids, *The Journal of Immunology*, 1231-1237 (1997).

Yachi et al., Distribution of liposomes containing mannobiose esters of fatty acid in rats, *J. Microencapsulation*, 12(4)377-388 (1995).

Perin et al., Evaluation of possible interference of antiinflammatory drugs upon scintigraphic imaging with macrophage targeting 99mTc-J001X: effects of methylprednisolone, dexamethasone, indomethacin and methotrexate, *Nucl. Med. Biol.*, 21(8)1093-1100 (1994).

Talmon, Transmission electron microscopy of complex fluids: The state of the art, *Ber. Bunsenges. Phys. Chem.*, 100:364-372 (1996).

Delpheyroux et al., A poliovirus neutralization epitope expressed on hybrid Hepatitis B surface antigen particles, *Science*, 233:472-475 (1986).

Aspinall, "The variable surface glycollpids of mycobacteria: Structures, synthesis of epitopes, and biological properties", *Advances in Carbohydrate Chemistry and Biochemistry*, 51:169-243 (1995).

\* cited by examiner

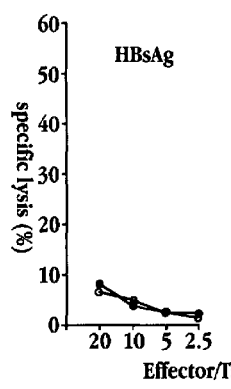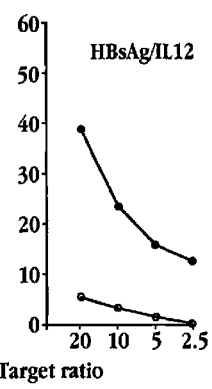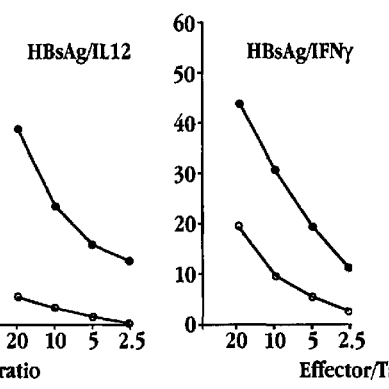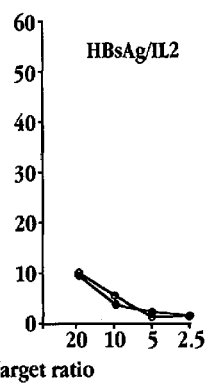
Fig. 6A   Fig. 6B   Fig. 6C   Fig. 6D
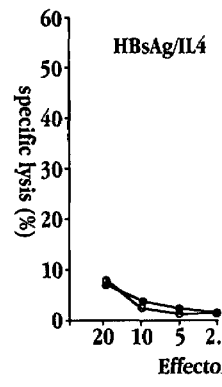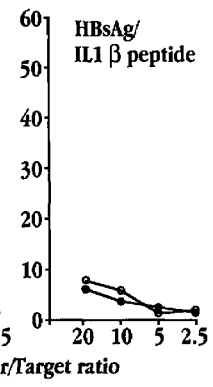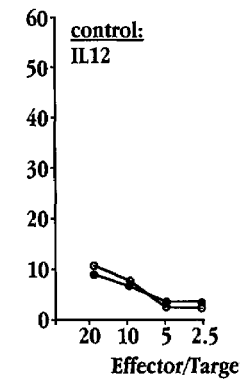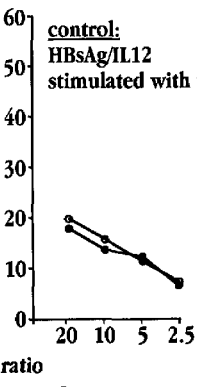
Fig. 6E   Fig. 6F   Fig. 6G   Fig. 6H

DELIVERY OF IMMUNOGENIC MOLECULES VIS HBSAG PARTICLES

The present application claims priority to U.S. provisional application 60/073,476, filed Feb. 3, 1998, which is hereby incorporated by reference.

FIELD OF THE INVENTION

The present invention relates to compositions in which a biologically active molecule, such as an antigenic peptide, a cytokine, or an oligonucleotide, is contained in an HBsAg particle, and to therapeutic uses of such compositions, particularly for enhancing the immunogenic activities of the components.

REFERENCES

Aspinall, G. O. et al., *Adv. Carbohydr. Chem. Biochem.* 51:169–242 (1995).

Clarke, B. E. et al., *Nature* 330(26):381–4 (1987).

Delpeyroux, F. et al., *Science* 233:472–81 (1986).

Diminsky, D. et al., *Vaccine* 15(6/7):637–647 (1997).

Felgner, P. L. et al., *Biochemistry* 20(8):2168–2172 (1981).

Francis, M. J. et al., *Proc. Natl. Acad. Sci. USA* 87:2545–9 (1990).

Geissler, M. et al., *J. Immunol.* 158(3):1231–7 (1997).

Lowry, O. H. et al., *J. Biol. Chem.* 193:265–275 (1951).

Nguyen, T. D. et al., *Cancer. Immunol. Immunother.* 43(6): 345–54 (1997).

Perin, F. et al., *Nucl. Med. Biol.* 21(8): 1093–100 (1994).

Puzo, G., *Crit. Rev. Microbiol.* 17(4):305–27 (1990).

Schirmbeck, R. et al., *J. Immunol.* 152(3):1110–1119 (1994).

Talmon, Y., *Ber. Bunsenges. Phys. Chem.* 100(3):364–72 (1996).

Weiner, G. J. et al., *Proc. Natl. Acad. Sci. USA* 94(20): 10833–7 (1997).

Wong, M. et al., *Biochemistry* 23:6498–6505 (1984).

Wooldridge, J. E. et al., *Blood* 89(8):2994–8 (1997).

Yachi, K. et al., *J. Microencapsul.* 12(4):377–88 (1995).

Yamamoto, S. et al., *J. Immunol.* 148(12):4072–6 (1992).

Yamamoto, T. et al., *Antisense Res. Dev.* 4(2): 119–22 (1994).

BACKGROUND OF THE INVENTION

Conventional vaccines against infectious viruses or microorganisms frequently employ inactivated or live-attenuated pathogen. Disadvantages of such vaccine preparations include difficulty in large-scale production, safety considerations in handling, and the risks involved in immunizing elderly or immunodeficient individuals with live-attenuated vaccines.

Subunit vaccines, which utilize isolated components of a virus particle, are a safer alternative to conventional vaccines. The components are typically recombinant proteins or synthetic short peptides. However, most subunit vaccines, like most soluble antigens, generally elicit only a humoral immune response, which stimulates B-lymphocytes to produce antibodies. Such a response is effective in attacking bacteria and viruses in the extracellular media, but not in the elimination of intracellular bacteria, parasites and virus-infected cells. For maximum effectiveness, a vaccine should also be able to elicit a CTL (cytotoxic T-lymphocyte) response. The CTL response stimulates the production of "killer" T-lymphocytes, which attack cells perceived as abnormal, including virus-infected cells.

The mode of processing and presentation of an antigen determines which T cell subtype (helper or cytotoxic) is activated during the immune response. In the exogenous (Class II) pathway, exogenous antigens enter an antigen presenting cell (APC) via endocytosis or a related mechanism. The proteins then undergo proteolysis, yielding peptides having 10–20 amino acids, which bind to MHC-II molecules. The resulting complexes stimulate CD4+ (helper) T cells, which regulate humoral immune responses. In the endogenous (Class I) pathway, proteins present in the cytoplasm, such as viral proteins, are degraded to peptides 8–10 amino acids in length, which bind to MHC-I molecules. The resulting complexes interact with CD8+ (cytotoxic) T-lymphocytes (CTL). As noted above, this response is especially important for protection against virus-infected cells or intracellular microorganisms.

Accordingly, it is desirable to provide immunogenic compositions which produce an effective CTL immune response, particularly for use with soluble antigens.

SUMMARY OF THE INVENTION

The present invention includes, in one aspect, a method of stimulating, enhancing or modulating an immune response to an antigen in a mammalian subject, by administration of an effective amount of a composition of the antigen contained in an HBsAg particle. In a preferred embodiment, the immune response is a CTL response, and is enhanced, preferably by a factor of two or more, relative to that elicited by the molecules when administered without HBsAg. The subject compositions are also effective to produce a CTL response when the antigenic molecule, administered without HBsAg, is substantially ineffective in producing such a response.

The HBsAg particle is preferably a recombinant particle, either yeast-derived or produced in a mammalian cell, such as a CHO (Chinese hamster ovary) cell. The encapsulated molecule is preferably an antigenic protein or peptide. Specific embodiments include those in which the molecule is ovalbumin or HIVenv/V3 peptide. In additional embodiments, the composition further includes an immunostimulating molecule, such as a cytokine or immunostimulating oligonucleotide, contained in the HBsAg particle.

In another aspect, the invention provides a method of stimulating, enhancing or modulating an immune response to HBsAg in a mammalian subject, by administration of an effective amount of a composition of an immunostimulating molecule contained in an HBsAg particle. In a preferred embodiment, the immune response is a CTL response, and the subject is a nonresponder at the CTL level when administered HBsAg particles without the immunostimulating molecule. Preferably, the immunostimulating molecule is a cytokine, such as IL-12, IL-10, or IFN-γ; IL-12 and IFN-γ are particularly preferred. Other immunostimulating molecules include cholera toxin (CT) protein, staphylococcal enterotoxin B (SEB) protein, and immunostimulating oligonucleotides.

Also provided is an immunogenic composition, comprising an HBsAg particle, and contained therein, a biologically active molecule. The composition is preferably prepared by incubating the particles in an aqueous medium in the presence of the molecule. In a preferred embodiment, the molecule is an antigen, e.g. HIVenv/$K^d$ peptide. In other preferred embodiments, the molecule is an immunostimulating compound, or the particle may contain both an antigen and an immunostimulating molecule. Preferred immunostimulants include a cytokines, such as IL-10, IL-12 or IFN-γ, and immunostimulating oligonucleotides. Other immunostimulating molecules which may be used include cholera toxin (CT) protein and staphylococcal enterotoxin B (SEB) protein.

The composition may also include a glycolipid incorporated into the external face of the lipid bilayer of the HBsAg particle, where the glycolipid preferably includes at least one mannose residue.

The invention also provides, in another aspect, a method of incorporating a biologically active molecule into an HBsAg particle. According to the method, the particles are incubated in an aqueous medium in the presence of the molecule. The temperature of incubation is preferably between about 35° C. and about 60° C., and more preferably between about 55° C. and about 60° C. The method may also include incorporating a glycolipid into the exterior surface of the HBsAg particle, preferably co-incubating the glycolipid with the HBsAg particles and biologically active molecule.

These and other objects and features of the invention will become more fully apparent when the following detailed description of the invention is read in conjunction with the accompanying drawings.

BRIEF DESCRIPTION OF THE DRAWINGS

FIG. 1 (A+B) shows a computer generated image of a cryotransmission electron micrograph of an HBsAg particle, showing the structure of the porous lipid vesicle having defined protein pores;

FIG. 2 (A+B) is a topographical image of an HBsAg obtained from image analysis of a cryotransmission electron micrograph of the particle;

FIG. 3 shows the ratio of total protein area to area of 24 kd+27 kd proteins, as determined by gel electrophoresis, of HBsAg alone and HBsAg incubated with ovalbumin at a series of increasing temperatures;

FIG. 4A shows the level of anti-HBsAg CTL response induced by cells stimulated with HBsAg alone, with OVA alone, and with OVA encapsulated in HBsAg, against HBsAg-specific cells (P815/S) and nonspecific cells (P815);

FIG. 4B shows the level of anti-OVA CTL response induced by cells stimulated as for FIG. 4A, against OVA-specific cells (EG7) and nonspecific cells (EL4);

FIG. 4C shows the level of anti-HBsAg antibody response induced by HBsAg alone, OVA alone, and OVA encapsulated in HBsAg;

FIG. 4D shows the level of anti-OVA antibody response induced by the compositions shown for FIG. 4C;

FIG. 5A shows the level of anti-HBsAg CTL response induced by cells stimulated with HBsAg alone, with HIV envV3-peptide alone, and with HIV envV3-peptide encapsulated in HBsAg, against HBsAg-specific cells (P815/S) and nonspecific cells (P815);

FIG. 5B shows the level of anti-HIV envV3-peptide CTL response induced by cells stimulated as for FIG. 5A, against HIV envV3-peptide-specific cells (P815/HIV envV3-peptide) and nonspecific cells (P815); and FIGS. 6A–H show the level of anti-HBsAg CTL response induced in cells of 'nonresponder' mice (C57BL/6H2-b) by HBsAg alone (A), HBsAg containing various cytokines (B–F), and IL-12 alone (G), and by HBsAg/IL-12 in a control experiment (H) in which the effector cells were restimulated with non-antigen-bearing cells.

DETAILED DESCRIPTION OF THE INVENTION

I. Hepatitis B Surface Antigen (HBsAg)

A. Background

Hepatitis B virus (HBV) is a major cause of acute and chronic hepatitis in humans. During HBV replication, a large excess (1000:1) of "empty" surface particles, containing neither capsids nor viral DNA/RNA, are produced. These HBsAg (hepatitis B surface antigen) particles are potent immunogens in humans and many animal species. First generation HBV subunit vaccines included HBsAg particles purified from the plasma of human chronic carriers. Due to the limited supply of carrier plasma and major safety problems, vaccines based on recombinant HBsAg particles derived from yeast (*Sacchromyces cerevisiae*) were introduced. More recently, a third generation recombinant HBV vaccine, which better resembles the human-derived particles, was introduced. These HBsAg particles are derived from Chinese hamster ovary (CHO) cells in culture and are referred to herein as CHO-HBsAg particles.

B. Structure

The composition, structure and immunogenicity of yeast- and CHO-derived HBsAg particles have been described (Diminsky et al.). The particles are about 20–33 nm in size and are composed of about 60% protein and 40% lipid by weight. Phospholipids are the predominant lipids. The CHO-derived particle differs primarily from the yeast-derived particle in that it includes three HBsAg surface proteins (each in two forms of glycosylation), designated large (L), medium (M) and small (S), while the latter includes only the nonglycosylated S peptide.

Biochemical analysis revealed that almost all (approx. 85%) HBsAg particle phospholipids are hydrolyzed by phospholipases A2 and C, and all aminophospholipids react with trinitrobenzene sulfonate (Diminsky). These observations suggested that the particle is not a sealed vesicle, but rather exists in the form of (a) a lipoprotein, having a monolayer of polar lipids coating a core of neutral lipids and part of the protein, or (b) a porous vesicle whose pores are permeable to the above reagents. Cryotransmission electron microscopy (FIG. 1) confirmed the latter possibility, showing, at a resolution of 1 nm, a porous vesicle.

Phospholipids cover large areas of the outer and inner protein component of the particle, but some protein domains loop out of the lipid layer and are accessible to antibodies or proteases. The particles are hollow, encapsulating a space of about 900–8200 cubic nm per particle. Access to the interior of the particles is mediated by the pores, which have an average diameter of about 1–2 nm.

FIGS. 2A and 2B show topographical images of HBsAg particles, each about 22 nm in diameter, obtained by image analysis of cryotransmission electron micrographs of the particles. (For a review of TEM methods see Talmon, 1996.) Such image analysis can be carried out using software provided by NIH or Adobe Systems Inc. Regions of higher density in the image were assigned higher values along the vertical (out of plane) axis, as shown in FIGS. 2A–2B. As represented in the Figures, the center of each vesicle contains an aqueous phase (lighter regions, having small numeric values). Proteins (darkest regions, having highest numeric values) are embedded in the lipid bilayer (medium tone regions). Pores in the bilayer can be clearly seen, as indicated by arrows in the Figures.

II. Encapsulation of Antigens in HBsAg Particles

In accordance with the present invention, it has been found that biologically active molecules, such as antigenic proteins and peptides, oligonucleotides, or cytokines, may be encapsulated in the hollow HBsAg particles, by virtue of the pores described above. As used herein, the terms "encapsulated in" or "contained in" indicate a physical containment or entrapment of the molecules, rather than a covalent linkage, as is found in fusion proteins, discussed further below. This containment refers both to molecule encapsulated within the interior of an HBsAg particle and to entrapped molecule which is exposed or present at the surface of the particle, by virtue of its porous structure.

The resulting compositions produce enhanced immune responses to the encapsulated antigenic molecules. In particular, the present compositions can stimulate a CTL response, which is enhanced, up to factors of five, ten or more, relative to that elicited by the antigenic molecules when administered without HBsAg. Such enhancement can be evaluated, for example, by percent lysis of specific cells relative to nonspecific control cells, using standard assays, as described below. The subject compositions can be effective to produce a CTL response even when the molecule, without HBsAg, is substantially ineffective in producing such a response (i.e., little or no CTL response is noted in target cells relative to control cells). As described below in Section III, encapsulation of immunostimulating molecules, such as cytokines, in HBsAg particles greatly enhances the immunogenicity of the HBsAg particles themselves.

These effects are demonstrated, in the experiments described below, for a protein having several hundred amino acids (ovalbumin), a small antigenic peptide (HIV/3, the third variable domain of the HIV gp120 envelope protein), and several immunostimulants (cytokines).

These examples are not intended to be limiting, and the invention includes HBsAg compositions incorporating other biologically active molecules. Particularly useful, as demonstrated herein, are compositions incorporating antigens or immunostimulating compounds, for the purpose of eliciting an enhanced humoral and cellular immune response. Specific examples of molecules useful in the compositions and methods of the invention include cytokines such as IL-6, IL-7, IL-10, IL-12, IL-15, IL-18, GM-CSF, and IFN-γ, immunostimulating oligonucleotides, genetically modified toxin molecules of tetanus, diphtheria, pertussis, and enterobacteria, malaria CS protein, HIV reverse transcriptase, nucleoprotein and matrix proteins of many viruses, and oncogenic viral proteins.

It is important to distinguish the present compositions, which comprise molecules encapsulated in HBsAg particles, from HBsAg-antigen fusion peptides described previously (e.g. Clarke et al., Francis et al., and Delpeyroux et al.). Such compositions are prepared by covalently linking the peptides, or, more typically, via chimeric DNA constructs. The latter approach requires preparing a chimeric DNA containing genes expressing the antigen and the desired HBV protein(s), introducing the fused construct into an appropriate expression vehicle, expressing the fusion protein, and isolating the protein. Delpeyroux et al. reported that titers obtained by immunizing mice with HBsAg-polio fusion protein were "low by poliovirus standards." A loss of the immune response against native HB was also observed, probably resulting from distortion of the HBsAg epitopes in the fusion protien. Clarke et al. reported significant anti-FMDV (foot and mouth disease virus) titers for an FMDV-HBsAg fusion protein but did not report a CTL response.

The present compositions, in contrast, are prepared by simple incubation of the components, not involving covalent modification. They were found to stimulate significant antibody and CTL responses, as detailed below.

A. Encapsulation of OVA (Ovalbumin) in HBsAg

HBsAg particles were incubated in the presence of OVA protein (100 μg each in 100 μl $H_2O$) at 4° C. (on ice), 37° C. and 56° C. At the end of 10 min., samples were cooled to 4° C., and the particles were isolated by ultrafiltration. In control experiments, OVA was incubated under identical conditions in PBS buffer, with no HBsAg particles present, and HBsAg particles were incubated under identical conditions without OVA. The OVA/HBsAg collected after ultrafiltration was analyzed by gel electrophoresis, and the protein in each band was quantified (Diminsky, Lowry). Because OVA overlaps with the PRE S1 (large protein) band of HBsAg, both having a MW of approximately 42 kD, analysis was done by comparing total density (39 kD+42 kD+45 kD) to that of the two S peptides (24 kD+27 kD).

Figure 3:
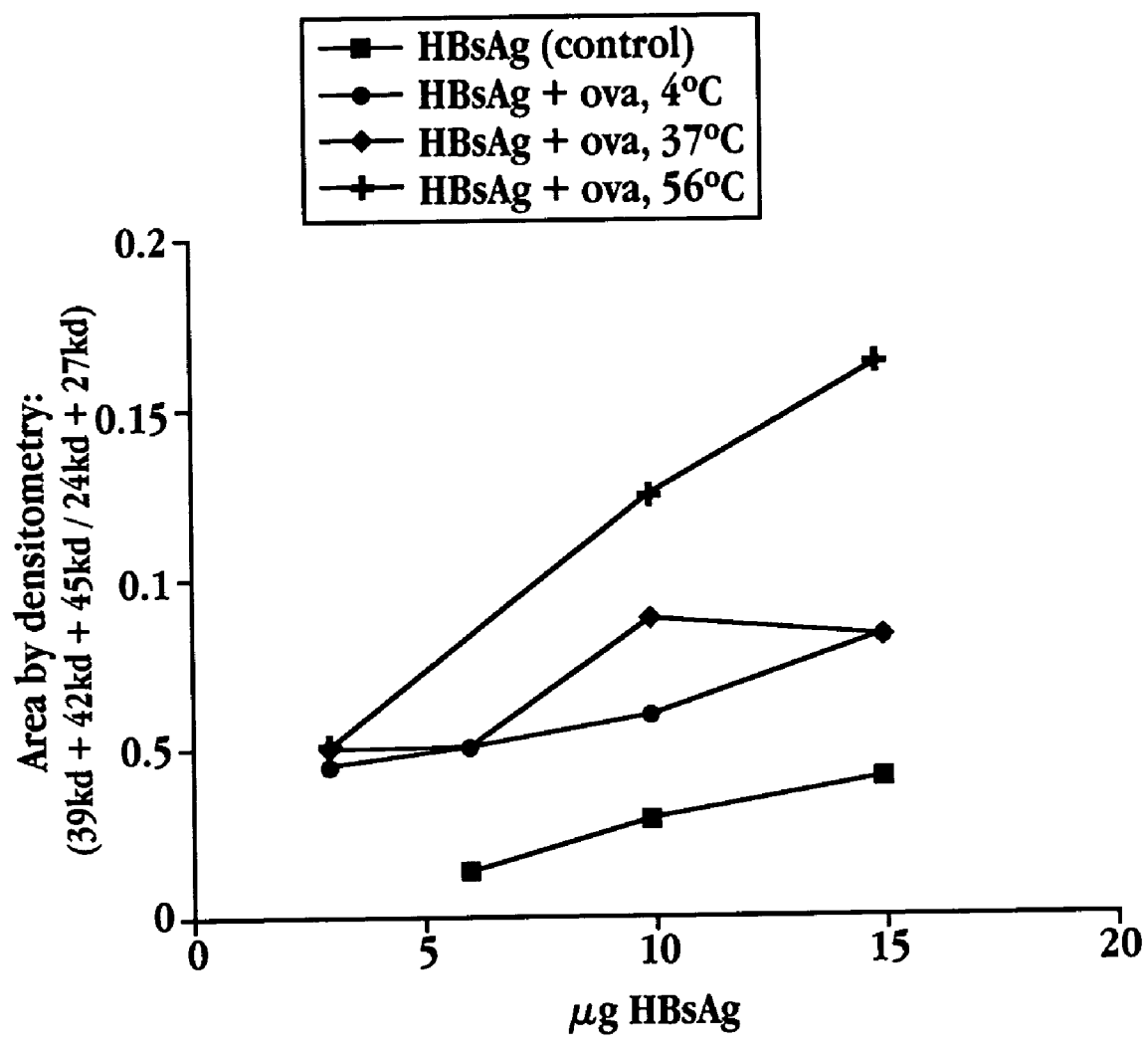

As shown in FIG. 3, the density ratio, and thus the presence of OVA, increased with increasing temperature of incubation. This effect could be due to an effective expansion, or increased flexibility, of the pores on the surface of the particles with increasing temperature. Quantitative analysis revealed about 6% OVA encapsulation at 56° C. Incubation temperatures much in excess of this, e.g. approaching 80° C., should be avoided, as the compositions are unstable at these temperatures.

B1. Induction of a CTL Response to Molecules Encapsulated in HBsAg Particles: OVA OVA/HBsAg particles, prepared as described above, were isolated, washed, and adjusted to the appropriate concentration for immunization. The following compositions were injected into F1 (H-2d/b) mice, each in 50 μl PBS (phosphate buffered saline): (a) 1 μg HBsAg particles (without adjuvants); (b) 100 μg native OVA; and (c) 1 μg HBsAg/OVA, as described in Section A above.

Figure 4A:
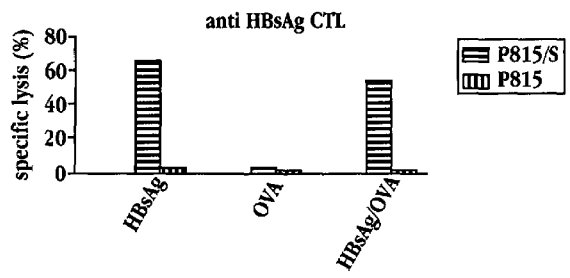
Figure 4B:
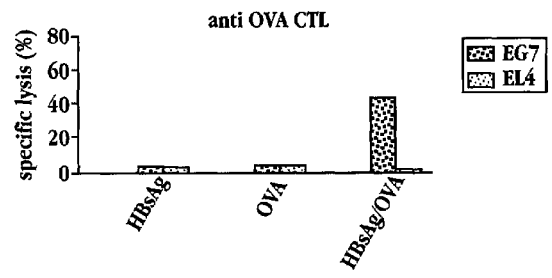
Figure 4C:
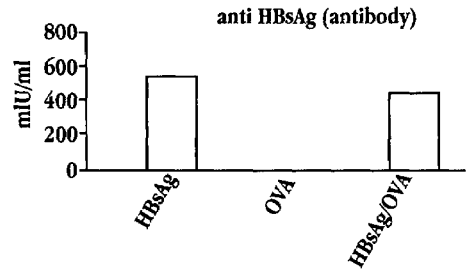
Figure 4D:
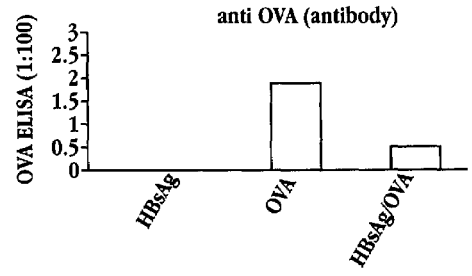

FIGS. 4A and 4B show the humoral (serum antibody) response and CTL response, respectively, elicited by each of these compositions, against HBsAg and against OVA. For evaluation of the CTL response, spleen or lymph nodes cells, obtained from immunized mice seven days to five weeks post-vaccination, were specifically restimulated in vitro for five days with syngeneic, irradiated OVA- or HBsAg-peptide-pulsed tumor cells. (The latter cells had been incubated in vitro with the recombinant HBsAg particles for 2 hours at 37° C.) The cells were harvested and tested in a 4-hour $^{51}Cr$ release cytolytic assay against antigen-bearing and non-antigen-bearing syngeneic targets. Lysis of cells specific for the HBsAg S protein (P815/S), or for OVA (EG7), was compared to that for nonspecific cells (P815 or EL4, respectively). The EG7 cells are EL4 cells which have been stably transfected with an expression plasmid encoding OVA.

As shown in the figures, composition (a), HBsAg alone, evoked both a CTL response and a humoral response against HBsAg. OVA alone elicited a humoral response but no CTL response.

HBsAg-encapsulated OVA, composition (c), elicited a strong anti-HBsAg humoral and CTL response and a weak anti-OVA humoral response. Most significantly, the composition also elicited a strong anti-OVA CTL response, where none was seen with OVA alone.

B2. Induction of CTL Response to HBsAg-Encapsulated Molecules: HIVenv/V3 Peptide In a similar set of experiments, BALB/c (H-2d) mice were immunized with the following compositions: (a) 1 μg HBsAg particles (without adjuvants); (b) 100 μg antigenic HIVenv/V3 peptide; and (c) 1 µg HBsAg containing antigenic HIVenv/V3 peptide. This composition was formed by co-incubation of the components, generally as described for OVA, above. It was estimated that approximately 20 ng peptide was incorporated per µg of HBsAg particles.

Figure 5A:
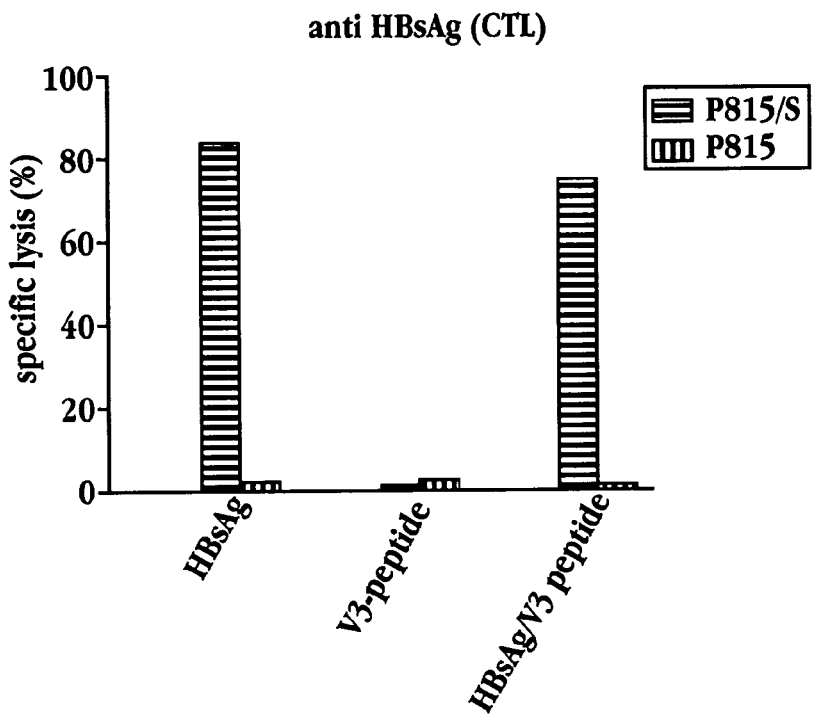
Figure 5B:
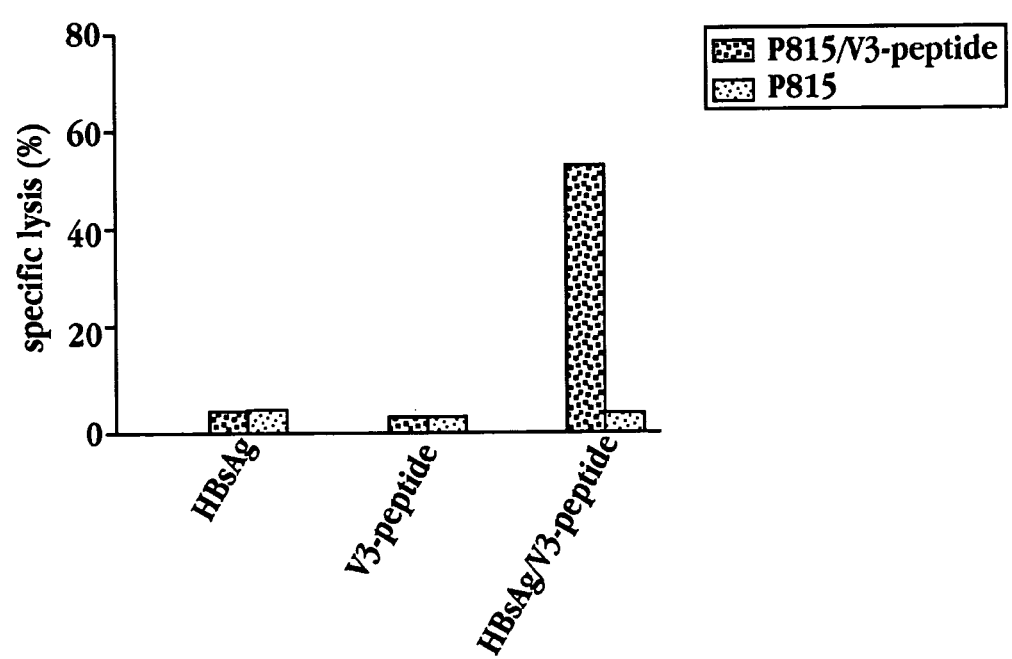

The CTL response was measured in specific cells (P815/S, as described above, for HBsAg, and P815/V3-peptide for HIVenv/V3 peptide) vs. that in nonspecific P815 cells. The results are shown in FIG. 5.

As shown in the Figure, both HBsAg alone and HBsAg/HIVenv/V3 elicited a strong anti-HBsAg CTL response. Furthermore, while HIVenv/V3 peptide alone (composition (b)) elicited no specific CTL response, a strong anti-HIVenv/V3 CTL response was seen for the peptide delivered in HBsAg (composition (c)).

These results show that proteins and peptides can be delivered to antigen-presenting cells (APC) in vivo by HBsAg particles for processing and immunogenic presentation via the Class I pathway, thus stimulating CTL precursors. This CTL response is elicited even for antigens that are not immunogenic for CTL when injected as native proteins.

In a related embodiment of this method, codelivery of antigen and cytokine in HBsAg can be employed to modulate the type of immune response primed or enhanced by a HBsAg/antigen formulation. For example, IL-12 drives CD4+ T-cell response polarization towards the Th1 phenotype and suppresses the Th2 phenotype. In contrast, IL-10 suppresses Th1-type response and enhances Th2-type response. Such compositions are useful when it is desired to modulate the pathogenic phenotype of an autoimmune or allergic T-cell response. For example, in treatment of autoimmune disease, it is often desirable to shift the phenotype of the immune response, rather than suppressing the response entirely.

III. Modulation of CTL Response by Immunostimulants Encapsulated in HBsAg Particles HBsAg particles, without adjuvants, induce a CTL response in $H-2^d/L^{d+}$ (BALB/c, C.B-17) mice. Other strains of mice, e.g. $H-2^d/L^{d-}$ (dm2) and $H-2^b$ (C57BL/6) mice, however, were found to be nonresponders (Schirmbeck et al.). It has been found, in accordance with the present invention, that encapsulation of immunostimulating molecules, e.g. cytokines, in HBsAg particles can induce a CTL response even in these 'nonresponder' strains.

HBsAg particles can also be used to deliver immunostimulatory oligonucleotides. Such a composition enhances the immunogenicity of the HBsAg for B cells (i.e., the antibody response) as well as T cells (CTL response). For example, oligonucleotides containing certain palindromic sequences were found to induce IFN and augment NK cell activity of mouse spleen cells (Yamamoto et al., 1992, 1994). Other oligonucleotides have been effective as adjuvants in inducing production of cytokines, activating B cells, monocytes, dendritic cells, and NK cells (Weiner; Wooldridge).

To produce the data shown in FIG. 6, several cytokines were loaded into HBsAg particles, following a protocol such as outlined above for OVA, with incubation carried out at 45° C. It was estimated that approximately 10 ng of cytokine was incorporated per µg of HBsAg particles (about 1% incorporation) at this temperature. Groups of 'nonresponder' mice ($H-2^b$ C57BL/6) were immunized with HBsAg particles, with and without incorporated cytokines, or with cytokine alone (FIG. 6G), in the amounts shown below:

A: 1 µg 'naked' HBsAg particles

B–F: 1 µg HBsAg/cytokine, where the cytokine was:
(b) IL-12, (c) IFN-γ, (d) IL-2, (e) IL-4,
(f) IL-1 β peptide G: 1 µg IL-12 (control)

H: 1 µg HBsAg/IL-12

After 12 days, splenocytes from the immunized mice were restimulated in vitro for 5 days with HBsAg-pulsed, syngeneic irradiated RBL5 lymphoma cells. For control experiment H, the splenocytes were restimulated with non-pulsed, syngeneic RBL5 cells. The splenocytes (effector cells) were then cocultured with $^{51}$Cr-labeled target cells, and the CTL response was measured by a standard $^{51}$Cr release assay. The target cells were either non-pulsed EL4 cells (open circles in FIGS. 6A–G), or EL4 cells which had been pulsed with HBsAg (solid circles).

Results are shown in FIGS. 6A–H. In the control experiments (A and G), where the "nonresponder" mice were immunized with HBsAg alone or IL-12 alone, no CTL response was seen in the HBsAg-specific cells as compared to the control cells. Nor was any response seen in experiment H, in which the splenocytes were restimulated with non-antigen-bearing RBL5 cells.

Compositions D–F showed a similar lack of response. The lack of response from HBsAg encapsulating IL4 (E) is not unexpected, as this cytokine is known to suppress the CTL response (see, for example, Nguyen, Geissler).

A strong CTL response was seen, however, for compositions B and C, where the cytokines were IL-12 and IFN-γ, respectively. This data shows that encapsulation of certain cytokines in HBsAg particles can induce a CTL response even in "nonresponder" strains; i.e., in subjects which do not show a CTL response to HBsAg alone.

In further experiments, the immunostimulating proteins cholera toxin (CT) and staphylococcal enterotoxin B (SEB), known as adjuvants for stimulation of CTL and humoral immune responses, were each incorporated into HBsAg particles, at a level of about 5–20 ng protein per µg HBsAg. Preliminary experiments testing the immunogenicity of these compositions showed a striking enhancement of the CTL and antibody responses of the HBsAg particles.

IV. Incorporation of Glycolipids into the Outer Surface of HBsAg Particles

Glycolipids can be introduced into the HBsAg particle exterior membrane by lipid exchange, using either micelles or liposomes, as described in Felgner. In Felgner, co-incubation of ganglioside micelles (containing predominantly trisialoganglioside GT1b) with fused phosphatidyl choline vesicles, about 70 nm in diameter, or SUV, about 20 nm in diameter, resulted in incorporation of ganglioside on the outer surface of the vesicles. Alternatively, the glycolipids can be introduced by the use of a glycolipid exchange protein, as described in Wong et al.

By such inclusion of glycolipids, particularly glycolipids containing available mannose residues, the particles may be targeted to specific antigen presenting cells, such as dendritic cells or macrophages. See, for example, Yachi, where modification of the surface of liposomes with fatty acid esters of mannobiose was found useful in targeting the liposomes to Kupffer cells and other macrophages. Perin et al. have employed an acylated poly-(1,3)-galactoside for the targeting of macrophages.

The surface glycolipids of mycobacteria have been well characterized (see e.g. Aspinall, Puzo). These glycolipids, which are often species-specific, have been used for the identification of various species, such as *M. leprae* and *M. tuberculosis*, and for monitoring treatment of disease caused by these organisms. In accordance with the present invention, HBsAg having a specific glycolipid incorporated into the lipid monolayer may be administered to induce a CTL response against mycobacteria-infected, syngeneic cells.

V. Administration

For use in humans, a preferred dose of encapsulated antigen is in the range of 0.01 to 20 µg, more preferably 0.02 to 2 µg, incorporated at about a 1 to 10 weight percent level in HBsAg particles. When HBsAg itself is the antigen, a preferred dose is in the 0.1 to 10 µg range, with about 1 to 10 weight percent of incorporated immunostimulant (e.g. cytokine). Administration may be by injection, e.g., intraperitoneal (ip), subcutaneous (sc), intravenous (iv), or intramuscular (im).

While the invention has been described with reference to specific methods and embodiments, it will be appreciated that various modifications may be made without departing from the invention.

What is claimed is:

1. A method of stimulating or enhancing a CTL response to a biologically active molecule in a mammalian subject in need of such CTL response stimulation and enhancement, comprising administering to said subject by injection into the body of said subject, in a manner so as to elicit a CTL response, an effective amount of a composition comprising the biologically active molecule, either entrapped within the interior of an HBsAg particle or exposed or present at the surface of an HBsAg particle by incubating said HBsAg particle at a temperature of about 35° C. to about 60° C. in an aqueous medium in the presence of the biologically active molecule, wherein said biologically active molecule is not covalently attached to said HBsAg particle, and wherein said CTL response is enhanced relative to that produced by the biologically active molecule alone.

2. The method of claim 1, wherein said biologically active molecule, when administered without said HBsAg particle, is substantially ineffective in producing a CTL response in said subject.

3. The method of claim 1, wherein said HBsAg particle is a recombinant HBsAg particle derived from a mammalian cell.

4. The method of claim 1, wherein said biologically active molecule is antigenic.

5. The method of claim 1, wherein said biologically active molecule is an antigenic protein or peptide.

6. The method of claim 5, wherein said antigenic protein or peptide is HIVenv/V3 peptide.

7. The method of claim 5, wherein said composition further comprises, in addition to the biologically active molecule, an immunostimulating molecule entrapped within or exposed or present at the surface of said HBsAg particle.

8. The method of claim 7, wherein said immunostimulating molecule is a cytokine.

9. The method of claim 7, wherein said immunostimulating molecule is an immunostimulatory oligonucleotide.

10. The method of claim 1, wherein said injection is selected from the group consisting of intraperitoneal, subcutaneous, intravenous, and intramuscular injection.

11. A composition comprising an HBsAg particle, a biologically active molecule either entrapped within the interior of an HBsAg particle or exposed or present at the surface of an HBsAg particle, and in addition to the biologically active molecule an immunostimulating molecule either entrapped within the interior of said HBsAg particle or exposed or present at the surface of said HBsAg particle, wherein said biologically active molecule is not covalently attached to said HBsAg particle.

12. The composition of claim 11, wherein said biologically active molecule is an antigen.

13. The composition of claim 11, wherein said biologically active molecule is antigenic.

14. The composition of claim 12, wherein said biologically active molecule is HIVenv/$K^d$ peptide.

15. The composition of claim 11, wherein said immunostimulating molecule is a cytokine.

16. The composition of claim 11, wherein said immunostimulating molecule is an immunostimulatory oligonucleotide.

17. The composition of claim 11, wherein said immunostimulating molecule is cholera toxin (CT) protein or staphylococcal enterotoxin B (SEB) protein.

18. The composition of claim 11, further comprising a glycolipid incorporated into the exterior surface of the lipid bilayer of said HBsAg particle.

19. The composition of claim 11, wherein said composition is prepared by incubating said particle in an aqueous medium in the presence of said biologically active molecule and said immunostimulating molecule.

20. A method of incorporating a biologically active molecule into an HBsAg particle, comprising a step of incubating said particle at a temperature of about 35° C. to about 60° C. in an aqueous medium in the presence of said molecule.

21. The method of claim 20, further comprising a step of incorporating a glycolipid into the exterior surface of said HBsAg particle.

22. The method of claim 21, wherein said incorporating step comprises co-incubating said glycolipid with said HBsAg particles and said biologically active molecule.

* * * * *